(12) United States Patent
Dahlström et al.

(10) Patent No.: US 9,248,007 B2
(45) Date of Patent: Feb. 2, 2016

(54) SET OF DENTAL COMPONENTS

(75) Inventors: Mattias Dahlström, Billdal (SE); Anders Halldin, Mölndal (SE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/450,587

(22) Filed: Apr. 19, 2012

(65) Prior Publication Data

US 2012/0270180 A1    Oct. 25, 2012

Related U.S. Application Data

(60) Provisional application No. 61/477,332, filed on Apr. 20, 2011.

(30) Foreign Application Priority Data

Apr. 20, 2011 (EP) .................................. 11163215

(51) Int. Cl.
*A61C 8/00* (2006.01)

(52) U.S. Cl.
CPC .............. *A61C 8/005* (2013.01); *A61C 8/0066* (2013.01); *A61C 8/0069* (2013.01)

(58) Field of Classification Search
CPC ...... A61C 8/005; A61C 8/006; A61C 8/0068; A61C 8/0069; A61C 8/0071; A61C 8/0072; A61C 8/0066
USPC ......................................... 433/172–176, 201.1
See application file for complete search history.

(56) References Cited

U.S. PATENT DOCUMENTS

| | | | |
|---|---|---|---|
| 5,344,457 A * | 9/1994 | Pilliar et al. ..................... 606/60 |
| 5,759,035 A * | 6/1998 | Ricci .............................. 433/174 |
| 5,989,026 A | 11/1999 | Rogers et al. |
| 6,283,753 B1 * | 9/2001 | Willoughby ................... 433/172 |
| 6,827,575 B1 * | 12/2004 | Jorneus .......................... 433/174 |
| 2005/0181330 A1 * | 8/2005 | Kim et al. ..................... 433/173 |
| 2008/0182227 A1 | 7/2008 | Wolf et al. |
| 2008/0227057 A1 * | 9/2008 | Anitua Aldecoa ............ 433/174 |

* cited by examiner

*Primary Examiner* — Edward Moran
(74) *Attorney, Agent, or Firm* — David A. Zdurne; Douglas J. Hura; Leana Levin

(57) ABSTRACT

According to an aspect of the invention, in a set of male dental components, such as abutment screws, each male dental component has a threaded portion with different core diameter. Each male dental component is to be connected to a mating female dental component, such as an abutment. The smaller core diameter a threaded portion has, the higher friction is provided when the male dental component is finally tightened to its mating female dental component, even though the same insertion torque is applied to all male dental components.

1 Claim, 9 Drawing Sheets

SET OF DENTAL COMPONENTS

RELATED APPLICATIONS

This patent application claims the benefit of and priority to U.S. Provisional Patent Application Ser. No. 61/477,332, filed on Apr. 20, 2011 and EP Patent Application Ser. No. 11163215.4, filed on Apr. 20, 2011, which are herein incorporated by reference for all purposes.

TECHNICAL FIELD

The present invention relates to a set of male dental components. The invention also relates to a set of female dental component. The invention also relates to a set of dental components comprising a subset of male dental components and a subset of female dental components.

BACKGROUND ART

A frequent way today to restore a damaged or lost tooth is to install a dental implant comprising a fixture in the adjacent jawbone tissue (maxilla or mandible) and replace the damaged or lost tooth with a dental prosthesis. A superstructure, such as an abutment, may be used as a connection between the dental prosthesis and the installed fixture.

An abutment may have an externally threaded portion formed in one piece with a prosthesis-supporting portion. The abutment is by means of its threaded portion screwed into the fixture which has an internal bore with a corresponding threaded portion. Thus, in this case, the abutment is a male dental component and the fixture is a female dental component.

An alternative to the one-piece abutment, is an abutment having a separate abutment screw. The abutment screw has an externally threaded portion and a screw head. When fastening the abutment to the fixture, the abutment is first mated to the fixture and then the abutment screw is inserted into a through-hole of the abutment so that the threaded portion of the abutment screw engages the internal threading of the fixture and the screw head is seated on a seat in the through-hole of the abutment. In this case the abutment screw may be regarded as a male dental component which is inserted into a female dental component in the form of an abutment.

Other examples of male/female dental components are bridge screws/bridge supports, guide pins, impression components and cylinders.

Manufacturers of dental components generally recommend a certain torque (normally in the region of 15-35 Ncm) to be used when the male dental component is finally tightened to the female dental component. For instance, a manufacturer may for a certain abutment screw recommend a torque of 25 Ncm when finally tightened to the abutment, typically when the screw head has touched the seat of the abutment.

If the applied torque is too low, the male dental component is not tightened adequately to the female dental component, which may lead to loosening of the male dental component. If loosened, the male dental component may in turn cause fractures in the female dental component.

On the other hand, if the applied torque is too high, the axially directed tensile stress becomes so high that the male dental component will break, the weakest point usually being below the first coronal revolution of the thread. The female dental component may also become damaged.

Unfortunately, dentists do not always use the recommended torque, but sometimes use a higher or a lower torque. Furthermore, a manufacturer may recommend different torques for different dental components or for different sizes of the same type of dental component. Thus, there is a risk of the dentist inadvertently applying a non-recommended torque.

An object of the invention is therefore to reduce the risk of dentists applying too low torques which may cause loosening of the male dental component and potentially ensuing fracturing of the female dental component, and also to reduce the risk of dentists applying too high torques with may cause the male dental component to break and potentially also damage the female dental component. This and other objects which will become apparent in the following, are accomplished by the invention as defined in the accompanying claims.

SUMMARY OF THE INVENTION

The invention is based on the insight that by only recommending one torque value, irrespectively of differences, such as different widths, between male dental components, the risk of a dentist mixing up the recommendations is reduced. The invention is further based on the insight that by modifying one or more features of an otherwise comparatively weak male dental component, such a component may be adequately tensioned with the same torque as a stronger male dental component. In particular, the invention is based on the understanding that part of the applied torque may be taken up by the friction between the male and female dental components, thereby reducing the tensile stress on the male dental component. Thus, if a first male dental component is more likely to break when finally tightened to a mating first female dental component than a second male dental component when finally tightened to a mating second female dental component, than a higher friction between the first male and female components will compensate for the relatively higher fragility of the first male dental component.

According to a first aspect of the invention, a set of male dental components is provided. The set comprises a first male dental component adapted to be connected to a mating first female dental component, the first male dental component comprising a threaded portion having a core provided with an external thread, a second male dental component adapted to be connected to a mating second female dental component, the second male dental component comprising a threaded portion having a core provided with an external thread, wherein the core of the threaded portion of said first male dental component has a smaller diameter than the core of the threaded portion of said second male dental component, and wherein, when finally tightened with the same torque to their respective mating female dental component, said first male dental component is configured and dimensioned to provide a higher friction against said first female dental component than the friction provided by the second male dental component against said second female dental component.

The first and second male dental components may, for instance, be abutment screws, one-piece abutments and bridge screws. The first and second female dental components may, for instance, be abutments provided with a through hole, dental fixtures and bridge supports.

The threaded portion of the male dental component is generally located at an apical portion of the male dental component. The external thread on the core presents axially alternating thread tops and thread bottoms. The width of the core of the threaded portion of the first male dental component is smaller than the width of the core of the threaded portion of the second male dental component. In other words the radial distance between the central axis and a thread bottom of the first male dental component is smaller than the radial distance between the central axis and a thread bottom of the second male dental component. The core of the threaded portion is normally cylindrical, although a slightly tapering core is also conceivable. For slightly tapering cores, the width of the core at the first revolution of the coronal end of the thread is smaller on the first male dental component than on the second male dental component.

According to at least one example embodiment, the external threads on the threaded portions of the first and second male dental components are adapted to engage with mating internal threads in the first and second female dental components, respectively. For instance, this is the case when the male dental components are in the form of one-piece abutments adapted to be screwed into a dental fixture.

According to at least one example embodiment, the external threads on the threaded portions of the first and second male dental components are adapted to engage with mating internal threads in first and second additional dental components. For instance, this is the case when the female dental components are abutments having a respective through-hole, and the male dental components are separate abutment screws for fastening the abutment to respective fixtures, the fixtures being said additional dental components.

The set of male dental components may comprise more than said first and said second male dental components. For instance, it may comprise a third male dental component adapted to be connected to a mating third female dental component, the third male dental component comprising a threaded portion having a core provided with an external thread, wherein the core of the threaded portion of said second male dental component has a smaller diameter than the core of the threaded portion of said third male dental component, wherein, when finally tightened with the same torque to their respective mating female dental component, said second male dental component is configured and dimensioned to provide a higher friction against said second female dental component than the friction provided by the third male dental component against said third female dental component.

Similarly, the set may comprise even more male dental components, such as a fourth, fifth, sixth, etc. male dental component adapted to be connected to respective female dental components.

The final tightening is understood to mean the tightening performed after the first and second dental components have come into final contact with each other, thereby creating a tensile stress in the male dental component. Thus, it should be understood that if a given torque is used when finally tightening the first male dental component to the first female dental component, then the friction between these first components is higher than the friction between the second male and female dental components if the same given torque would be used when finally tightening the second male dental component to the second female dental component.

Thus, despite the fact that the first male dental component has a thinner core at the threaded portion and would normally have been more likely to break than the second male dental component having a thicker core at the threaded portion, because the first male dental component provides a higher friction than what may normally be the case, the applied torque will result in a lower tensile stress to the first male dental component, thus reducing the risk of it breaking.

According to at least one example embodiment, each male dental component comprises a non-threaded seat-mating portion located coronally of said threaded portion, wherein said seat-mating portion forms a non-zero angle in relation to the longitudinal central axis of the male dental component, wherein the seat-mating portion of the first male dental component is configured and dimensioned to provide a higher friction against a mating seat of the first female dental component than the friction provided by the seat-mating portion of the second male dental component against a corresponding mating seat of the second female dental component.

The seat-mating portion may, for instance, be a tapering portion, wherein the angle in relation to the central axis is between 0-90°. The seat-mating portion may suitably taper in the apical direction. Alternatively, the seat-mating portion may be substantially perpendicular to the central axis, i.e. the angle may be about 90° relative to the central axis. Alternatively, the seat-mating portion may taper in the coronal direction.

The seat of the female component may suitably be dimensioned and configured to correspond to said seat-mating portion of the male dental component. Suitably, the seat of the female dental component and the seat-mating portion of the male dental component form the same angle relative to the central axis. For instance, the seat-mating portion of the first male dental component and the mating seat of the first female dental component may form an angle $\alpha$ in relation to the central axis, while the seat-mating portion of the second male dental component and the mating seat of the second female dental component may form an angle $\beta$ in relation to the central axis.

If said angle $\alpha$ is smaller than said angle then a higher friction is obtainable between the first male and female dental components then between the second male and female dental components. This is reflected in at least one example embodiment, according to which the seat-mating portion of the first male dental component forms a smaller angle in relation to the central axis than the seat-mating portion of the second male dental component.

When referring to said angle relative to the central axis, it should be understood that said referred angle is an acute angle or a 90° angle. To exemplify this, one can imagine a dial (clock face), being numbered in standard format from 1 to 12, wherein numeral 12 is at the top and numeral 6 is at the bottom. An imaginary straight line extending through numerals 6 and 12 may represent the axis of the male dental component. When the hand of the clock points at numeral 1 it will form an angle of 30° with the "axis". When the hand of the clock has moved to point at numeral 2 it forms an angle of 60° with the "axis". Finally, when the hand of the clock has moved to reference numeral 3 it forms a 90° angle with the "axis". Thus, this sequence represents seat-mating portions providing decreasing friction. The larger the angle the smaller the friction. However, when the hand of the clock continues and reaches numeral 4 it gets closer again to the "axis" and forms 60° with the "axis". Thus, this should not be regarded as an angle of 120°, because from a frictional point of view, a coronally tapering seat-mating portion of 60° can provide the same friction as an apically tapering seat-mating portion of 60°. Similarly, when continuing to reference numeral 5 on the dial, the angle will be 30°. Thus, when having passed the perpendicular direction to the axis, a seat-mating portion will increasingly provide higher friction when mated to a corresponding seat. A coronally tapering seat-mating portion of a male dental component and a corresponding coronally tapering seat of a female dental component may be advantageous, for instance, if the female dental component is a ceramic abutment. Such a coronal tapering would result in an inwardly directed pressure on the seat of the ceramic abutment (as opposed to an outwardly directed pressure caused by an apical tapering) which reduces the risk of cracks in the ceramic abutment.

Said seat-mating portion of a male dental component may suitably form an angle of 35°-45°, such as about 40° relative to the central axis. The seat-mating portion of another male dental component may suitably form an angle of 45°-55°, such as about 50° relative to the central axis. Other conceivable examples of the angle of such a seat-mating portion of a male dental component are: 55°-65°, such as about 60°; 65°-75°, such as about 70°; 75°-85°, such as about 80°; 85°-95°, such as about 90°. A set of male dental components may comprise at least two male dental components, each having a seat-mating portion with one of the above exemplified angles or within one of the above exemplified ranges of angles. Of course, a set may comprise three or more dental components having seat-mating portions with respective angles selected from the above ranges.

According to at least one example embodiment, the seat-mating portion of the first male dental component has a larger area which is intended for contact with the mating seat of the first female dental component than the area of the seat-mating portion of the second male dental component intended for contact with the mating seat of the second female dental component. An increased contacting area means a larger friction, even though the angles of the respective seat-mating portions are the same for the first and second male dental components. For instance, both the first and the second male dental component may have a seat-mating portion with a contacting surface forming an angle of 90° (i.e. flat-to-flat contact with the seat of the female dental component) with the central axis, but the area of the contacting surface of the first component being larger than that of the second component. The corresponding area differentiation is also conceivable for other angles, e.g. both the first and the second male dental component may have a seat-mating portion with a contacting surface forming an angle of 70° (i.e. cone-to-cone contact) with the central axis, but the area of the contacting surface of the first component being larger than that of the second component.

Another way to provide different frictional effect for the first and second male dental components is to provide the components with different surface properties. Thus, according to at least one example embodiment, each one of said male dental components has a contact surface for contacting its respective mating female dental component, wherein said contact surface of the first male dental component is different from said contact surface of the second male dental component, such that the coefficient of friction between said contact surface of the first male dental component and its mating first female dental component is higher than the coefficient of friction between said contact surface of the second male dental component and its mating second female dental component. The difference in coefficient of friction may, for instance, be achieved by surface modification, surface roughening, anodization or surface coating. The first male dental component may be surface modified in one way, while the second male dental component is not modified at all (e.g. smooth) or modified in another way. Said contact surface may be on a seat-mating portion. Alternatively, it may be on any other portion that contacts the female dental component, and may increase the friction compared to such a portion having a smooth surface.

Thus, according to at least one example embodiment, the coefficient of friction between the seat-mating portion of the first male dental component and (suitably the seat of) the mating first female dental component is higher than the coefficient of friction between the seat-mating portion of the second male dental component and (suitably the seat of) the mating second female dental component.

According to at least one example embodiment, the coefficient of friction between the threaded portion of the first male dental component and a mating internally threaded portion, e.g. in a fixture, is higher than the coefficient of friction between the threaded portion of the second male dental component and a mating internally threaded portion, e.g. in a fixture.

If the difference in coefficient of friction is due to different surface roughness, this may be accomplished by means of e.g. blasting, etching or any other suitable process known in the art.

Thus, according to at least one example embodiment the surface roughness of said seat-mating portion of the first male dental component is greater than the surface roughness of said seat-mating portion of the second male dental component.

According to at least one example embodiment, the surface roughness on the threaded portion of the first male dental component is larger than the surface roughness on the threaded portion of the second male dental component.

It is also conceivable to further differentiate the friction provided by the first and second male dental components by combining various friction increasing and/or friction reducing measures. For instance, according to at least one example embodiment, the seat-mating portion of the first male dental component forms a smaller angle in relation to the central axis than the seat-mating portion of the second male dental component and, additionally, the surface of the threaded-portion of the second male dental component is modified (e.g. by coating, polishing, etc) to provide a smaller friction than a non-modified threaded portion. For instance, the following situation may occur. The seat mating portion of the weaker first male dental component is assumed to form a non-zero angle <90°, such as 70°, with the central axis, while the seat-mating portion of the stronger second male dental component is assumed to form an angle of 90°. Thus, although the first male dental component will provide a higher friction than the second male dental component so that both of them will be installable with the same recommended torque, one may be of the opinion that the second male dental component is not adequately pre-stressed when it is in its final installed state. Therefore, by reducing the friction between the threaded portion of the second male dental component and a mating threaded portion, e.g. internally of a fixture, the pre-stressing is increased. As mentioned above, the friction reduction may be accomplished by modifying the surface of the threads of the second male dental component, e.g. by suitable coating, polishing, etc.

According to a second aspect of the invention, a set of female dental components is provided. The set comprises a first female dental component adapted to be connected to a mating first male dental component, the first male dental component comprising a threaded portion having a core provided with an external thread, a second female dental component adapted to be connected to a mating second male dental component, the second male dental component comprising a threaded portion having a core provided with an external thread, wherein the core of the threaded portion of said first male dental component has a smaller diameter than the core of the threaded portion of said second male dental component, and wherein, when said male dental components are finally tightened with the same torque to their respective female dental components, said first female dental component is configured and dimensioned to provide a higher friction against said first male dental component than the friction provided by the second female dental component against said second male dental component.

As mentioned in connection with the first aspect of the invention, also in the second aspect of the invention the first and second male dental components may, for instance, be abutment screws, one-piece abutments and bridge screws. The first and second female dental components may, for instance, be abutments provided with a through hole, dental fixtures and bridge supports.

According to at least one example embodiment, each female dental component comprises a seat for receiving the respective mating male dental component, wherein said seat forms a non-zero angle in relation to the longitudinal central axis of the female dental component, and wherein the seat of the first female dental component is configured and dimensioned to provide a higher friction against a corresponding seat-mating portion of the first male dental component than the friction provided by the seat of the second female dental component against a corresponding seat-mating portion of the second male dental component.

Similarly to the seat-mating portions of the male dental components discussed in connection with the first aspect of the invention, said seat of a female dental component may, for instance, be a tapering portion, wherein the angle in relation to the central axis is between 0-90°. Alternatively, the seat-mating portion may be perpendicular to the central axis, i.e. the angle may be about 90° relative to the central axis. Suitably, the seat of the female dental component and the seat-mating portion of the male dental component form the same angle relative to the central axis.

According to at least one example embodiment, the seat of the first female dental component forms a smaller angle in relation to the central axis than the seat of the second female dental component. The angle is measured in the same way as for seat-mating portions of the male dental components, which have been described in connection with the first aspect of the invention. Also, the angles and ranges of angles exemplified in connection with the first aspect of the invention are also applicable to the seats of the female dental components according to the second aspect of the invention.

According to at least one example embodiment, the seat of the first female dental component has a larger area which is intended for contact with the corresponding seat-mating portion of the first male dental component than the area of the seat of the second female dental component intended for contact with the corresponding seat-mating portion of the second male dental component. As described in connection with the first aspect of the invention, an increased contacting area means a larger friction, even though the angles of the respective seat-mating portions are the same for the first and second male dental components.

According to at least one example embodiment, each one of said female dental components has a contact surface for contacting its respective mating male dental component, wherein said contact surface of the first female dental component is different from said, contact surface of the second female dental component, such that the coefficient of friction between said contact surface of the first female dental component and the mating first male dental component is higher than the coefficient of friction between said contact surface of the second female dental component and its mating second male dental component.

Any features discussed in connection with the set according to the first aspect of the invention may be implemented as features in the set according to the second aspect of the invention.

According to a third aspect of the invention, a set of dental components is provided. The set comprises a subset of male dental components comprising a first male dental component and a second male dental component, and a subset of female dental components comprising a first female dental component and a second female dental component, wherein said first male dental component is adapted to be connected to said first female dental component, the first male dental component comprising a threaded portion having a core provided with an external thread, wherein said second male dental component is adapted to be connected to said second female dental component, the second male dental component comprising a threaded portion having a core provided with an external thread, wherein the core of the threaded portion of said first male dental component has a smaller diameter than the core of the threaded portion of said second male dental component, and wherein, when the male dental components are finally tightened with the same torque to their respective female dental components, the friction between said first male dental component and said first female dental component is higher than the friction between said second male dental component and said second female dental component.

In the set according to the third aspect of the invention, the subset of male dental components may have the corresponding features and embodiments as those comprised in the set according to the first aspect of the invention. Similarly, in the set according to the third aspect of the invention, the subset of female dental components may have the corresponding features and embodiments as those comprised in the set according to the second aspect of the invention.

Thus, according to at least one example embodiment, each male dental component comprises a non-threaded seat-mating portion located coronally of said threaded portion and each female dental component comprises a seat for receiving said seat-mating portion of the respective male dental component, wherein said seat-mating portion and said seat each forms a non-zero angle in relation to the longitudinal central axis of the respective dental component, and wherein, when the male dental components are finally tightened with the same torque to their respective female dental components, the friction between the seat-mating portion of the first male dental component and the seat of the first female dental component is higher than the friction between the seat-mating portion of the second male dental component and the seat of the second female dental component.

According to at least one example embodiment, the seat-mating portion of the first male dental component and the mating seat of the first female dental component form a smaller angle in relation to the central axis than the seat-mating portion of the second male dental component and the mating seat of the second female dental component.

According to at least one example embodiment, the contact area between the seat-mating portion of the first male dental component and the mating seat of the first female dental component is larger than the contact area between the seat-mating portion of the second male dental component and the mating seat of the second female dental component.

According to at least one example embodiment, each one of said male dental components has a contact surface for contacting a contact surface of its respective mating female dental component, wherein the coefficient of friction between said contact surface of the first male dental component and its mating first female dental component is higher than the coefficient of friction between said contact surface of the second male dental component and its mating second female dental component.

Any features discussed in connection with the sets according to the first and second aspects of the invention may be implemented as features in the set according to the third aspect of the invention.

Any one of the first, second and third aspects of the invention, includes at least one example embodiment according to which said female dental components are abutments adapted to be connected to a respective dental fixture insertable into a jawbone, wherein said male dental components are abutment screws for fastening the respective mating abutment to the respective dental fixture.

Any one of the first, second and third aspects of the invention, includes at least one example embodiment according to which each abutment screw comprises a screw head having an apical portion which forms a non-zero angle in relation to the central axis of the abutment screw, wherein said first male dental component is a first abutment screw and said second male dental component is a second abutment screw, wherein said first female dental component is a first abutment and said second female dental component is a second abutment, and wherein the apical portion of the screw head of the first abutment screw forms a smaller angle in relation to the central axis than the apical portion of the screw head of the second abutment screw, and/or wherein a seat of the first abutment for receiving the apical portion of the screw head of the first abutment screw forms a smaller angle in relation to the central axis than a seat of the second abutment for receiving the apical portion of the screw head of the second abutment screw.

Thus, the first abutment screw, having a thinner core, and thus being more fragile, will when connected to said first abutment provide a higher friction than the wider second abutment screw when connected to said second abutment. Thus, the first abutment screw may be adequately tensioned with the same torque as the stronger second abutment screw, because part of the applied torque is taken up by the friction between the first abutment and first abutment screws, thereby reducing the tensile stress on the first abutment screw.

It should be understood that, in this application, a dental implant may comprise a dental fixture and a superstructure, such as an abutment.

A dental fixture is for use as the anchoring member of a dental prosthesis. To this end, the dental fixture is insertable into a pre-prepared bore hole in the bone tissue of a jawbone (maxilla or mandible) at a site where the dental prosthesis is required. The dental fixture is normally rotated into the bore hole.

For screw-type dental fixtures the bore hole may be provided with internal threads in advance or may be left un-tapped with the dental fixture provided with a self-tapping capacity, e.g. by the provision of one or more axially-extending cutting recesses, edges or notches, etc in the fixture thread. For instance, an apical end portion of the fixture may be provided with 2-4 cutting recesses, such as 3 cutting recesses. Other number of cutting recesses are readily conceivable.

A superstructure for connecting a prosthetic part to the fixture may comprise an abutment, spacer or other transmucosal component which engages to the dental fixture to bridge the gingiva overlying the maxilla or mandible. The prosthetic part, e.g. a crown, bridge or denture may be secured to the abutment. There are various other forms that the superstructure can take.

The term "coronal" is here and throughout this application used to indicate a direction towards a head end or trailing end of the dental implant. For instance, in a situation where an abutment is connected to a dental fixture, the coronal direction of the abutment would be a direction towards the part of the abutment being directed away from the fixture. Conversely, the term "apical" indicates a direction towards an insertion or leading end of the component. Thus, apical and coronal are opposite directions. Furthermore, the terms "axial", "axial direction" or "axially" are used throughout this application to indicate a direction taken from the coronal end to the apical end, or vice versa. The terms "radial", "radial direction" or "radially" indicate a direction perpendicular to the axial direction.

A blind bore or socket may extend apically into the fixture body from the coronal end to an end surface in-between the apical and coronal ends of the fixture body for a superstructure to be secured to the fixture. The socket may comprise an internally-threaded section for screw connection of the superstructure to the fixture. A rotational lock for the superstructure may be provided in the socket, such as an internal polygonal side wall, e.g. hexagonal, or alternatively one or more protrusions from or indentation in the wall of the socket. A section of the socket, such as the coronal section, may be tapered towards the apical end. The tapered section is suitably arranged coronally of the internally-threaded section.

The fixture may be used in a one stage procedure or a two stage procedure. In a one stage procedure a healing or temporary abutment is connected to the fixture to form the gingival tissue, and after a healing period the healing or temporary abutment is replaced by a permanent abutment. For a two stage procedure the fixture is provided with a cover screw and the gingival tissue is sutured over the fixture and cover screw, and after a healing period the tissue is opened up and an abutment is connected to the fixture after removal of the cover screw.

The fixture may have a conically tapering end portion which tapers towards the coronal end. The axial extent of this coronal end portion is small compared to the total length of the fixture, as an example no more than 4% of the total length, such as in the range of 1.5%-3.7%. The coronal end portion may suitably be provided without a threaded surface, e.g. having a smooth or a roughened (such as blasted) surface.

The fixture may have a substantially flat coronal end surface which is perpendicular to the longitudinal axis of the fixture. Alternatively, the coronal end surface may have a sloped contour relative to the longitudinal axis of the fixture, e.g. such that when positioned within the jawbone the length of the fixture is larger on a lingual side and shorter on a buccal side of the fixture. Another alternative is a saddle-shaped or wave-like coronal end surface.

DETAILED DESCRIPTION OF THE DRAWINGS

FIGS. 1*a-b*, 2*a-b* and 3*a-b* illustrate a set of dental components comprising a subset of male dental components and a subset of female dental components according to at least some example embodiments.

Figures 1A, 1B:
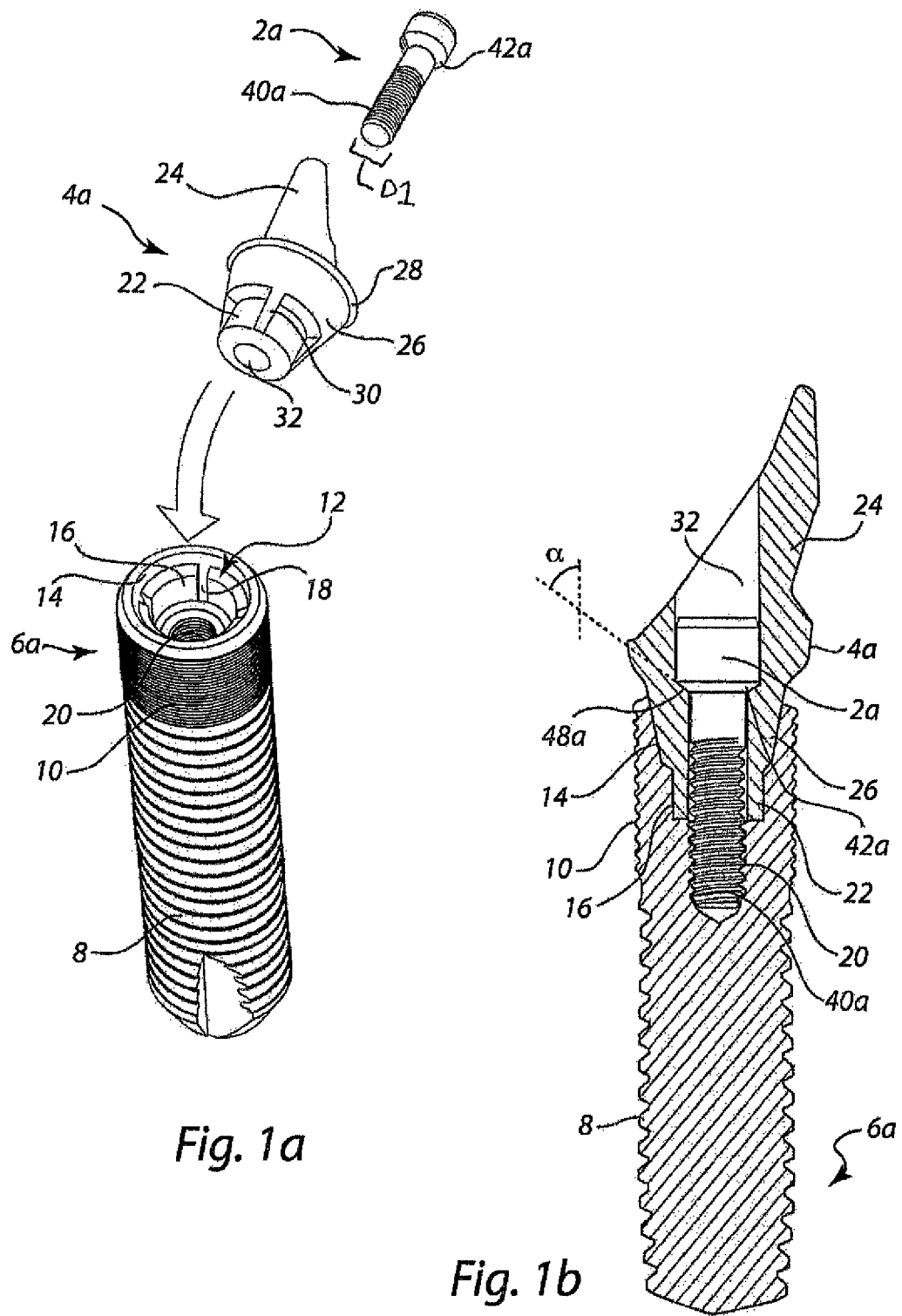
FIGS. 1a-b illustrate a set of dental components comprising a subset of male dental components and a subset of female dental components according to at least some example embodiments.

Starting with FIGS. 1*a*-1*b*, a male dental component, here in the form of an abutment screw 2*a* is adapted to be joined to a female dental component, here in the form of an abutment 4*a*, in order to fasten the abutment to a fixture 6*a*.

The fixture 6*a* is herein illustrated as having an exterior provided with relatively large threads 8 intended to engage cancellous bone tissue. A coronal portion of the fixture is provided with relatively small threads 10 having a smaller peak-to-peak distance intended to engage cortical bone tissue. The illustrated fixture 6*a* is just an example, and any other fixture exterior known in the art may be used for osseointegration of the fixture.

A socket 12 having an open end is provided in the coronal end of the fixture 6*a*. The socket 12 extends apically into the fixture 6*a*. The socket 12 is for receiving a dental component such as the illustrated abutment 4*a* which will bridge the gingiva overlying the bore-hole and support/present a prosthetic part. However, it may also receive other dental components such as an abutment replica, a driver, a healing cap or an impression pick-up element.

Although various alternative configurations are conceivable, the socket 12 is herein illustrated as having a conical coronal section 14 and a substantially cylindrical intermediate wall section 16. Four radially extending recesses 18 are provided in the intermediate wall section 16. The recesses 18 are herein illustrated as continuations of the conical coronal section 14 and are thus apically tapering. As an alternative, the recesses 18 may be non-tapering. Further as an alternative, the intermediate wall section 16 may be substantially conical.

The socket 12 is further provided with an internally threaded apical section 20.

The abutment 4*a* comprises an engagement portion 22, which is herein illustrated as having a generally cylindrical enveloping surface, although other enveloping surfaces, such as tapering, would be a conceivable alternatives. The abutment 4*a* further comprises a dental crown-receiving or prosthesis-receiving portion 24 which extends coronally of the fixture 6*a* above the gingiva. An extension portion 26, herein illustrated as coronally flaring up to a shoulder 28, is intended to extend through the gingiva and is provided between the engagement portion 22 and the prosthesis-receiving portion 24.

Four radial projections 30 are spaced around the cylindrical enveloping surface of the engagement portion 22. The four projections 30, which in other embodiments may be present in other numbers, are herein illustrated as wedge-like and apically tapering, i.e. their radial extension is largest at their coronal end.

The abutment 4*a* is provided with a through-hole 32, wherein the abutment screw 2*a* is adapted to be inserted into the through-hole 32 and engage the internal thread 20 of the fixture 6*a* in order to secure the abutment 4*a* to the fixture 6*a*.

In the illustrated example, the prosthesis-receiving portion 24 of the abutment 4*a* is angled relative to the axis of the through hole 32. The user, such as a dentist, is able to select which one of the four indexing positions provide the best orientation for the angled prosthesis-receiving portion 24. Likewise, if the prosthesis-receiving portion 24 is designed custom-fit and has a patient-specific configuration, the user will be able to arrange the abutment 4*a* in a desired indexing position with respect to the fixture 6*a*. Although, four recesses 18 in the socket 12 may be quite enough in many surgical applications, it is conceivable to provide a socket with more recesses to allow further indexing positions.

After the abutment 4*a* has been arranged in the desired rotational indexing position relative to the fixture 6*a*, and the projection/recess interfaces has provided a rotational lock, the abutment screw 2*a* is inserted through the through-hole 32 of the abutment 4*a* and into the internally threaded apical section 20 of the fixture 6*a* and is tightened. Finally, a prosthetic tooth (not shown) may be attached to the abutment 4*a*. The abutment screw 2*a* used has a relatively small diameter. This is because the fixture 6*a*, to which the abutment screw 2*a* is intended to fixate the abutment 4*a*, has a relatively small diameter, and to allow for a certain thickness of material around the socket 12. Comparison may be made to the fixtures in FIGS. 2*a-b* and 3*a-b*.

Figures 2A, 2B:
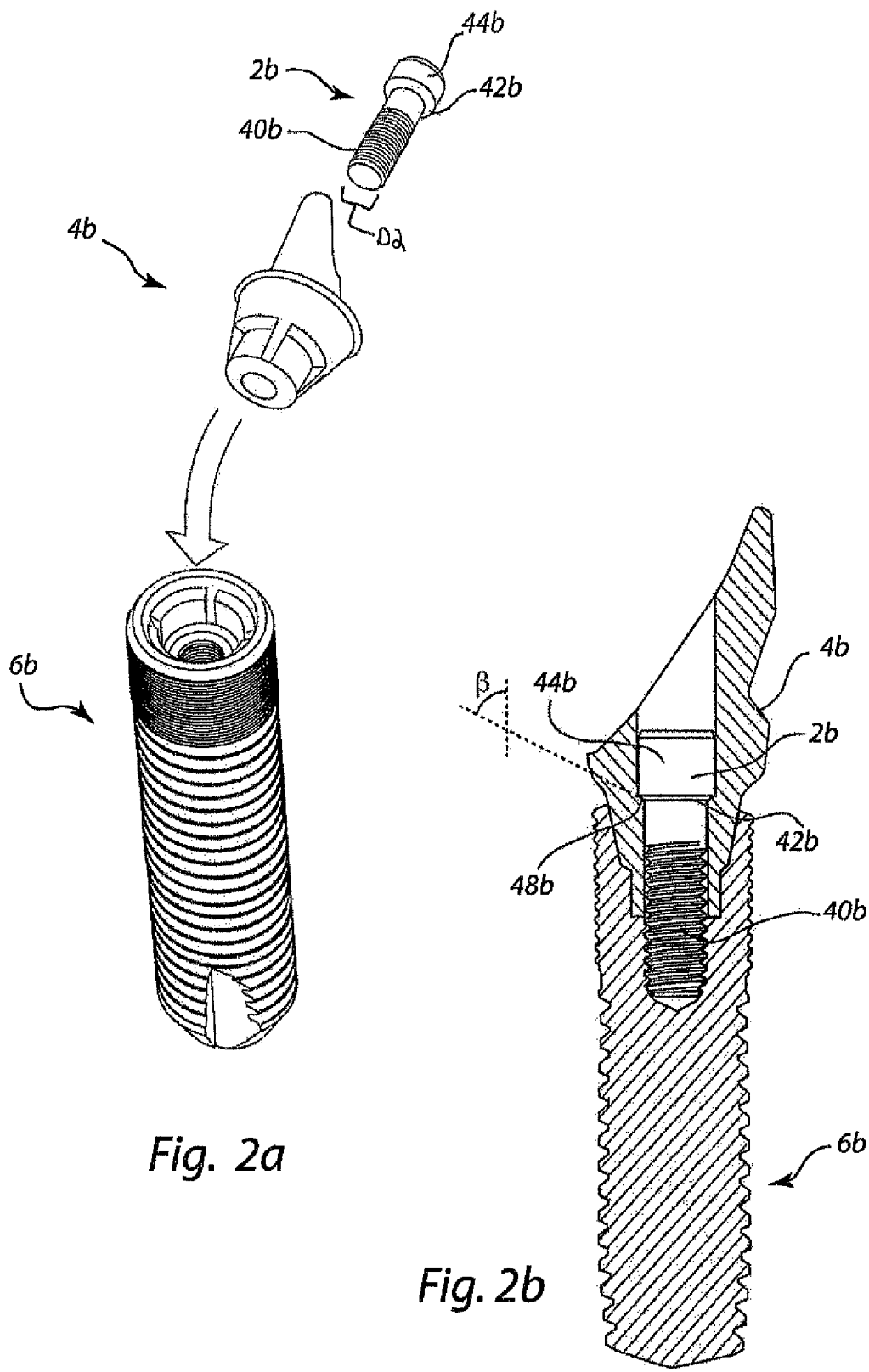
FIGS. 2a-b illustrate a set of dental components comprising a subset of male dental components and a subset of female dental components according to at least some example embodiments.

In FIGS. 2*a-b* a somewhat wider fixture 6*b* is illustrated, which allows for a somewhat wider abutment screw 2*b* to be used for fixating an abutment 4*b* to the fixture 6*b*.

Figures 3A, 3B:
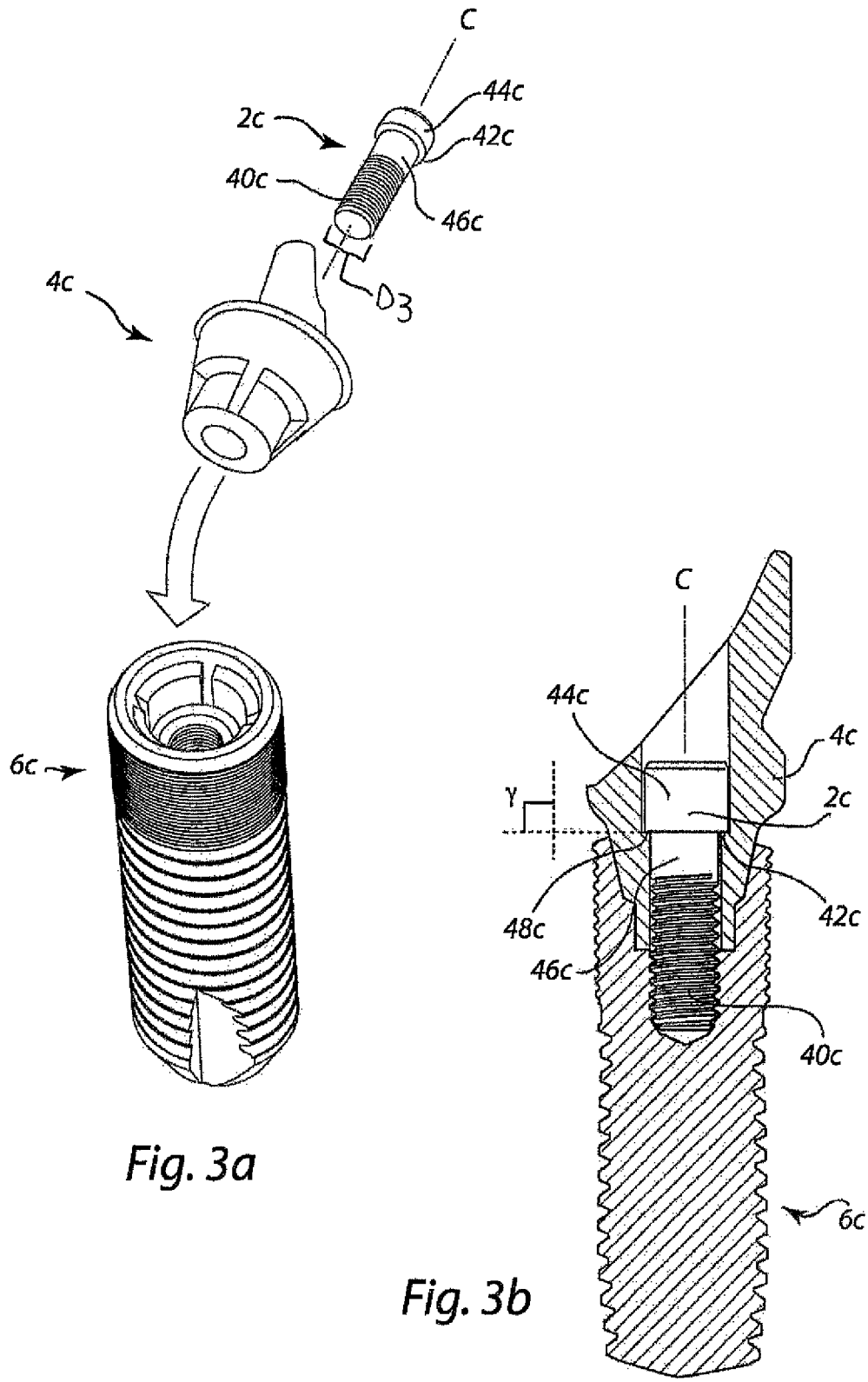
FIGS. 3a-b illustrate a set of dental components comprising a subset of male dental components and a subset of female dental components according to at least some example embodiments.

In FIGS. 3*a-b* an even wider fixture 6*c* is illustrated, thus allowing for an even wider abutment screw 2*c* to be used for fixating an abutment 4*c* to the fixture 6*c*.

Thus, with reference to FIGS. 1*a-b*, 2*a-b*, 3*a-b*, a set of male dental components in the form of abutment screws is disclosed and a set of female dental components in the form of abutments is disclosed. In the following, FIGS. 1*a-b* will be referred to as showing a first abutment screw 2*a* and a first abutment 4*a*, FIGS. 2*a-b* will be referred to as showing a second abutment screw 2*b* and a second abutment 4*b*, and FIGS. 3*a-b* will be referred to as showing a third abutment screw 2*c* and a third abutment 4*c*.

The first abutment screw 2*a* comprises a threaded portion 40*a* having a core provided with and external thread. The second abutment screw 2*b* comprises a threaded portion 40*b* having a core provided with an external thread, wherein the core of the threaded portion 40*a* of the first abutment screw 2*a* has a smaller diameter than the core of the threaded portion 40*b* of the second abutment screw 2*b*. The third abutment screw 2*c* comprises a threaded portion 40*c* having a core provided with an external thread, wherein the core of the threaded portion 40*b* of the second abutment screw 2*b* has a smaller diameter than the core of the threaded portion 40*c* of the third abutment screw 2*c*.

Each abutment screw 2*a*, 2*b*, 2*c* is provided with a head and a shaft, wherein the threaded portion 40*a*, 40*b*, 40*c* is at an apical portion of the shaft. In FIG. 3*b* it can be seen that the apical end 42*c* of the head 44*c* of the third abutment screw 2*c* is substantially perpendicular to the adjacent non-threaded portion 46*c* of the shaft. The apical end 42*c* is a seat-mating portion located coronally of the threaded portion 40*c* and forming an angle γ of about 90° in relation to the longitudinal central axis C of the third abutment screw 2c. The third abutment 4c has a corresponding abutment seat 48c for receiving the seat-mating portion 42c (in this case the apical end or underside of the head) of the third abutment screw 2c. The seat 48c of the third abutment 4c forms an angle γ of about 90° in relation to the longitudinal central axis C of the third abutment. Thus, when the third abutment screw 2c is inserted into the third abutment 4c for fixating the latter to the third fixture 6c, its seat-mating portion 42c will eventually come into contact with the seat 48c of the third abutment 4c. Because it will result in a flat-to-flat contact, any further and final tightening of the third abutment screw 2c will result in relatively low friction between the seat-mating portion 42c of the third abutment screw 2c and the seat 48c of the abutment 4c.

The second abutment screw 2b has, compared to the third abutment screw 2c, a smaller core diameter at the threaded portion 40b and its core is therefore more fragile. However, in order to compensate for the smaller dimension, the seat-mating portion 42b at the apical end of the head 44b of the second abutment screw 2b forms a smaller angle β relative to the central axis compared to said angle γ of the third abutment screw 2c. Similarly, the mating seat 48b of the second abutment 4b forms a corresponding smaller angle β in relation to the central axis. Thus, when the seat-mating portion 42b of the second abutment screw 2b has come into cone-to-cone contact with the mating seat 48b of the second abutment 4b, the final tightening will result in a higher friction between the seat-mating portion 42b of the second abutment screw 2b and the seat 48b of the second abutment 4b than the previously mentioned friction between the third abutment 4c and the third abutment screw 2c. Because the forces of the insertion torque are partly consumed by the larger friction, there will be a lower tensile strain on the threaded portion 40b of the second abutment screw 2b than if the seat-mating portion 42b and seat 48b would have formed the same 90° angle γ as for the third abutment 4c and third abutment screw 2c. In other words, with an adequate inclination of the seat-mating portion 42b and seat 48b of the second abutment 4b and abutment screw 2b, a dentist may apply the same insertion torque for the second abutment screw 2b as applied for the third abutment screw 2c, without risking breaking the second abutment screw 2b because of too high insertion torque.

Similarly, the first abutment screw 2a, which has an even narrower core at the threaded portion 40a, has a seat-mating portion 42a which has an even smaller acute angle α relative to the central axis and thus provides (with the same applied insertion torque) an even higher friction when the first abutment screw 2a is finally tightened to the first abutment 4a, the first abutment 4a having a mating seat 48a with the same angle α as the seat-mating portion 42a of the first abutment screw 2a. Thus, the relationship between said angles is α<β<γ.

It should be noted that, if it is found that the angles of the different abutment screws 2a, 2b, 2c are adequate, and yet one or more of the abutment screws are not enough pre-stressed after having been finally installed with the recommended torque, it is conceivable to reduce the friction of the threaded portion in order to increase the pre-stressing. For instance, if it is desired to have the third abutment screw 2c more pre-stressed to obtain a more firm fixation, the threaded portion 40c may be provided with a friction-reducing coating or be otherwise modified for reducing the friction against the fixture 6c.

Figures 4A, 4B, 4C:
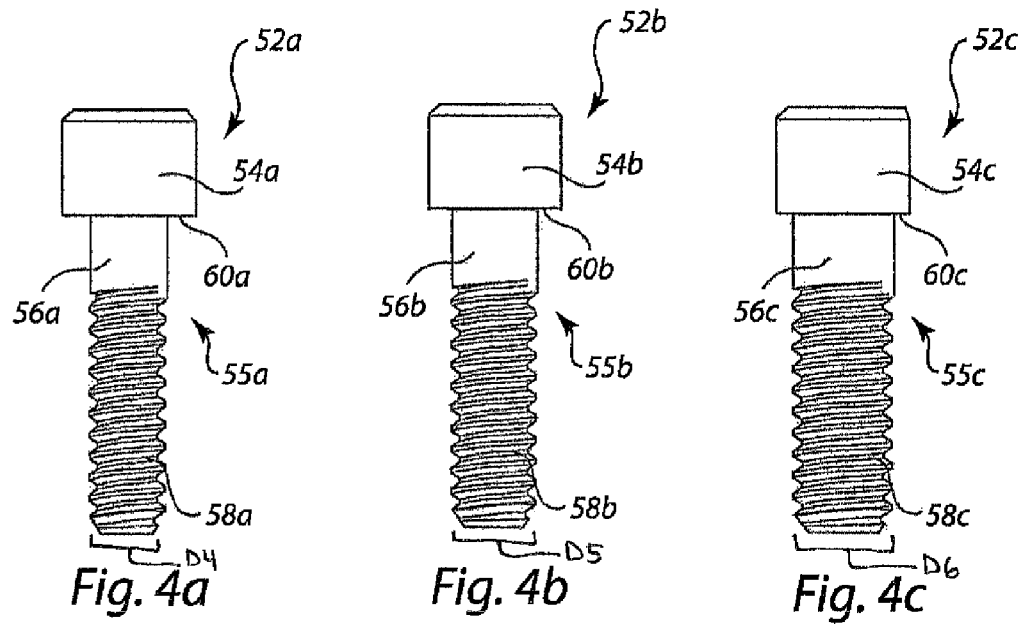
FIGS. 4a-4c illustrate a set of male dental components according to at least one example embodiment.

FIGS. 4a-4c illustrate a set of male dental components according to at least one example embodiment. The male dental components are here illustrated as abutment screws (or bridge screws). In the following, FIG. 4a will be referred to as showing a first abutment screw 52a, FIG. 4b will be referred to as showing a second abutment screw 52b, and FIG. 4c will be referred to as showing a third abutment screw 52c.

The third abutment screw 52c in FIG. 4c may, for instance, correspond to the previously discussed third abutment screw 2c in FIG. 3c. In other words, the third abutment screw 52c in FIG. 4c has a head 54c and a shaft 55c. The shaft 55c is provided with a coronal non-threaded portion 56c and an apical threaded portion 58c. The apical end or underside 60c of the head 54c is perpendicular to the shaft 55c and thus forms an angle of 90° with respect to the central axis of the third abutment screw 52c (and will act as said seat-mating portion as discussed in connection with the previous embodiments). Said underside 60c of the head 54c will act as a contact surface which will mate with a seat of a female dental component, such as an abutment. The maximum contact area presented by the underside 60c of the head 54c will thus be the diameter of the underside 60c of the head 54c minus the diameter of the coronal non-threaded portion 56c of the shaft 55c.

The second abutment screw 52b in FIG. 4b comprises a shaft 55b with a threaded portion 58b which has a smaller core diameter than the threaded portion 58c of the third abutment screw 52c. Thus, the threaded portion 58b of the second abutment screw 52b is more fragile than the threaded portion 58c of the third abutment screw 52c. However, in order to be able to use the same insertion torque as for the third abutment screw 52c, the second abutment screw 52b is configured and designed to provide a higher friction (which will take up some of the applied force) when finally tightened to its corresponding female dental component, thereby reducing the tensile strain on the threaded portion 58b of the second abutment screw 52b. This higher friction is accomplished by means of a larger area of the contact surface provided by the underside 60b of the head 54b of the second abutment screw 52b. Thus, the difference in diameter between the underside 60b of the head 54b and the coronal non-threaded portion 56b of the adjacent shaft 55b is larger for the second abutment screw 52b than for the third abutment screw 52c.

Similarly, the first abutment screw 52a, having a threaded portion 58a with an even smaller diameter, is compensated by having an underside 60a of the head 54a with an even larger contact surface for providing an even larger friction. Thus, the difference in diameter between the underside 60a of the head 54a and the coronal non-threaded portion 56a of the adjacent shaft 55a is larger for the first abutment screw 52a than for the second abutment screw 52b.

Thus, each one of the first, second and third abutment screws 52a, 52b, 52c may be connected to their respective female dental component using the same value of the insertion torque, without risking a too high tensile strain on the threaded portions 58a, 58b of the smaller first and second abutment screws 52a, 52b.

Figures 5A, 5B, 5C:
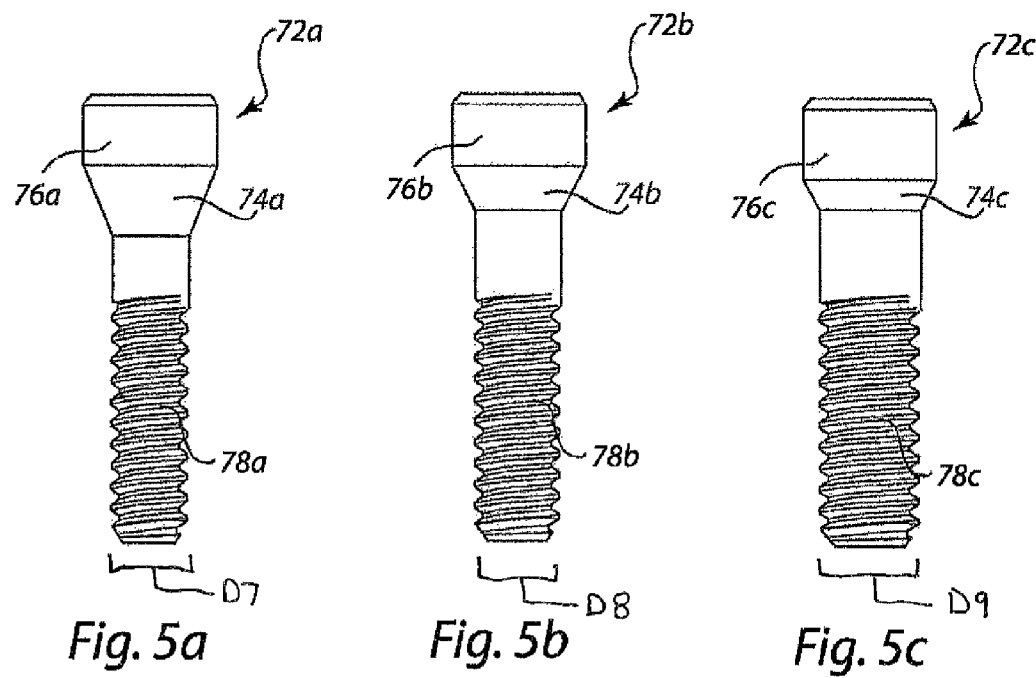
FIGS. 5a-5c illustrate a set of male dental components according to at least another example embodiment.

FIGS. 5a-5c illustrate a set of male dental components according to at least another example embodiment. The male dental components are herein exemplified as abutment screws 72a, 72b, 72c (or bridge screws). Unlike the perpendicular undersides 60a, 60b, 60c of the heads 54a, 54b, 54c of the abutment screws 52a, 52b, 52c in FIGS. 4a-4c, the undersides 74a, 74b, 74c of the heads 76a, 76b, 76c of the abutment screws 72a, 72b, 72c in FIGS. 5a-5c is apically tapering and thus forming an angle between 0-90° with respect to the central axis. However, similarly to the abutment screws 52a, 52b, 52c in FIGS. 4a-4c, the abutment screws 72a, 72b, 72c in FIGS. 5a-5c present differently dimensioned friction-proving contact surfaces. Thus, the first abutment screw 72a in FIG. 5a has the smallest diameter with respect to the core of the threaded portion 78a, and is therefore compensated with an underside 74a presenting the tapering contact surface having the largest area, i.e. providing the highest friction when the first abutment screw 72a is finally tightened to a mating female dental component. The second abutment screw 72b in FIG. 5b has a somewhat larger diameter with respect to the core of the threaded portion 78b, and therefore has an underside 74b with a somewhat smaller contact surface area, i.e. for providing a smaller friction than the first abutment screw 72a. Finally, the third abutment screw 72c in FIG. 5c has the largest diameter with respect to the core of the threaded portion 78c and therefore has an underside 74c presenting the tapering contact surface with the smallest area, i.e. providing the smallest friction.

Figure 6:
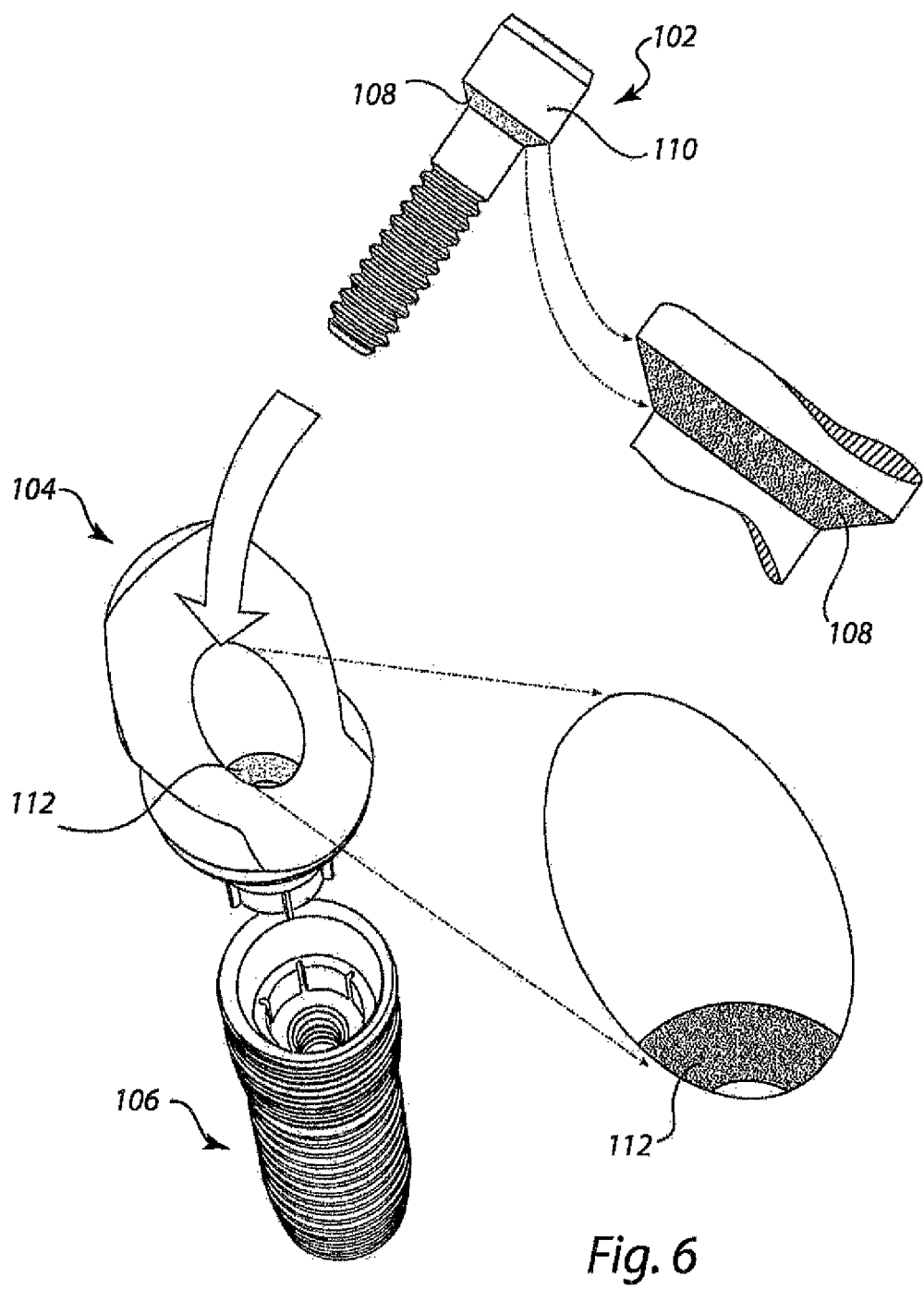
FIG. 6 illustrates surface modification of dental components for obtaining desired friction-affecting properties.

FIG. 6 illustrates surface modification of dental components for obtaining desired friction-affecting properties. Rather than providing male and female dental components within a set with different areas of contact surfaces or with different angles for achieving different frictional properties to compensate for the diameter differences with respect to the core of the threaded portion of the male dental component, variations in surface properties is another alternative. Thus, FIG. 6 illustrates an example in which the underside 108 (seat-mating portion) of the head 110 of an abutment screw 102 has been provided with a surface roughness, and similarly the mating seat 112 of the abutment 104 has been provided with a surface roughness. When the abutment screw 102 is finally tightened to the abutment 104 (after the abutment 104 has been inserted into the fixture 106) a higher friction will arise than if the seat-mating portion 108 and seat 112 would have been smooth surfaces. Thus, a first male dental component having a threaded portion with a smaller core diameter than a second male dental component, may advantageously be provided with a contact surface of greater surface roughness in order to provide more friction. It should be noted that to achieve a higher friction between the male and female dental components, it is not necessary that both components are provided with the greater surface roughness. Providing one of the components, e.g. the abutment screw 102 in FIG. 6 with roughened surface 108 while keeping the seat 112 of the abutment 104 smooth will still result in a higher friction than if both components would have smooth contact surfaces. Other surface modification alternatives are, of course conceivable, for affecting the frictional coefficients. Thus, instead of surface roughening, an alternative would be surface coating, another alternative would be anodization, etc.

FIGS. 7a-b, 8a-b and 9a-b illustrate a set of dental components comprising a subset of male dental components and a subset of female dental components according to at least some example embodiments. Here, the male dental components are represented by abutments 201a, 201b, 201c, while the female dental components are represented by dental fixtures 203a, 203b, 203c.

In the following, FIGS. 7a-b will be referred to as showing a first abutment 201a and a first fixture 203a, FIGS. 8a-b will be referred to as showing a second abutment 201b and a second fixture 203b, and FIGS. 9a-b will be referred to as showing a third abutment 201c and a third fixture 203c.

Figures 7A, 7B:
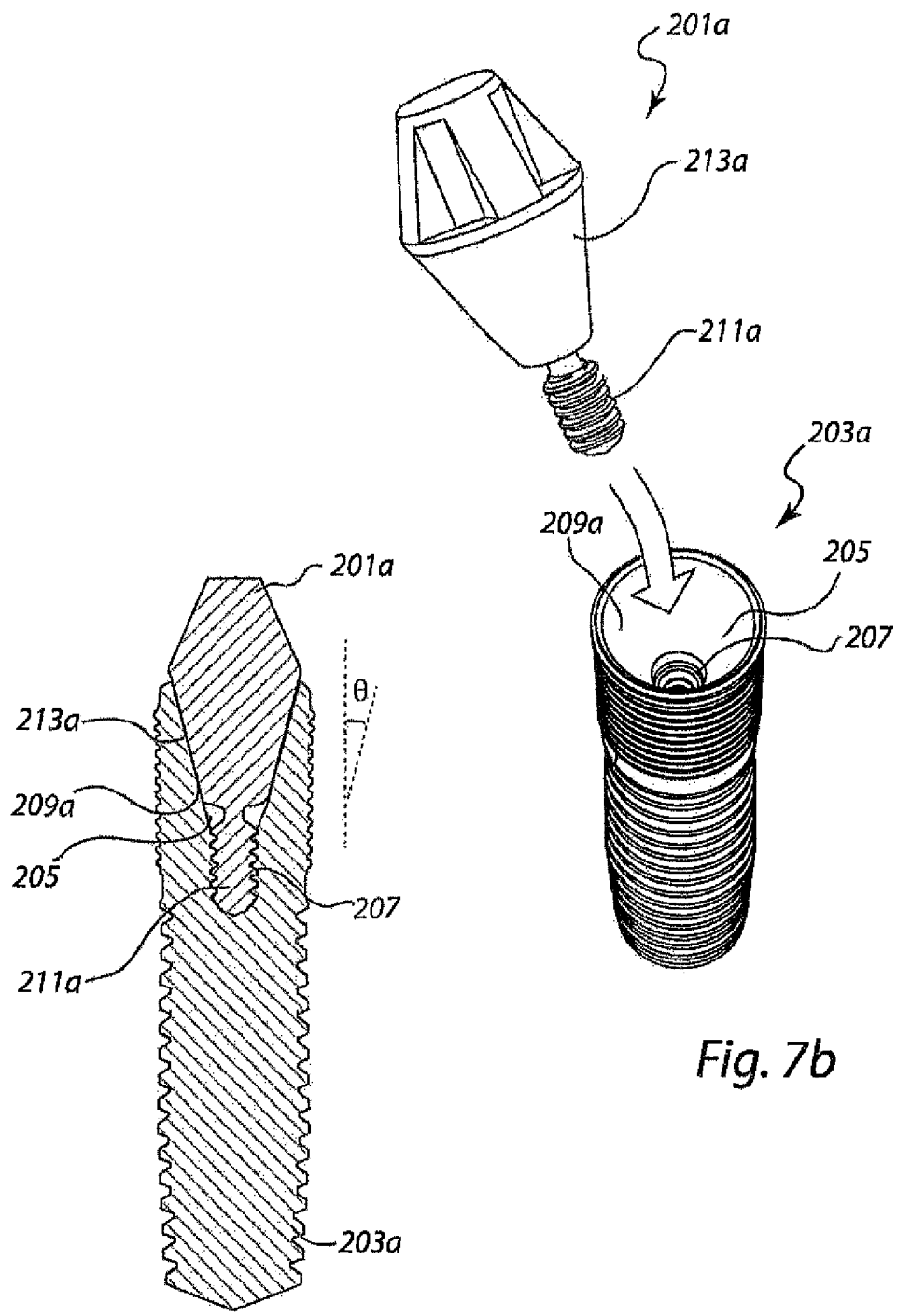
FIGS. 7a-b illustrate a set of dental components comprising a subset of male dental components and a subset of female dental components according to at least some example embodiments.

Starting with FIGS. 7a-b, the first fixture 203a has at its coronal end a socket 205 with an apical threaded portion 207 and a coronal tapering portion 209a which serves as a seat 209a for the first abutment 201a. The seat 209a forms a non-zero angle θ with respect to the longitudinal central axis of the first fixture 203a. The first abutment 201a is provided with an apical threaded portion 211a, which is formed in one piece with the abutment 201a and which is intended to be screwed into the threaded portion 207 of the first fixture 203a. The core of the threaded portion 211a of the first abutment 201a has a relatively small diameter. The first abutment 201a also has an apically tapering seat-mating portion 213a for mating with said seat 209a of the first fixture 203a. When the first abutment 201a is finally tightened to the first fixture 203a, the seat-mating portion 213a will together with the mating seat 209a provide a relatively large friction.

Figures 8A, 8B:
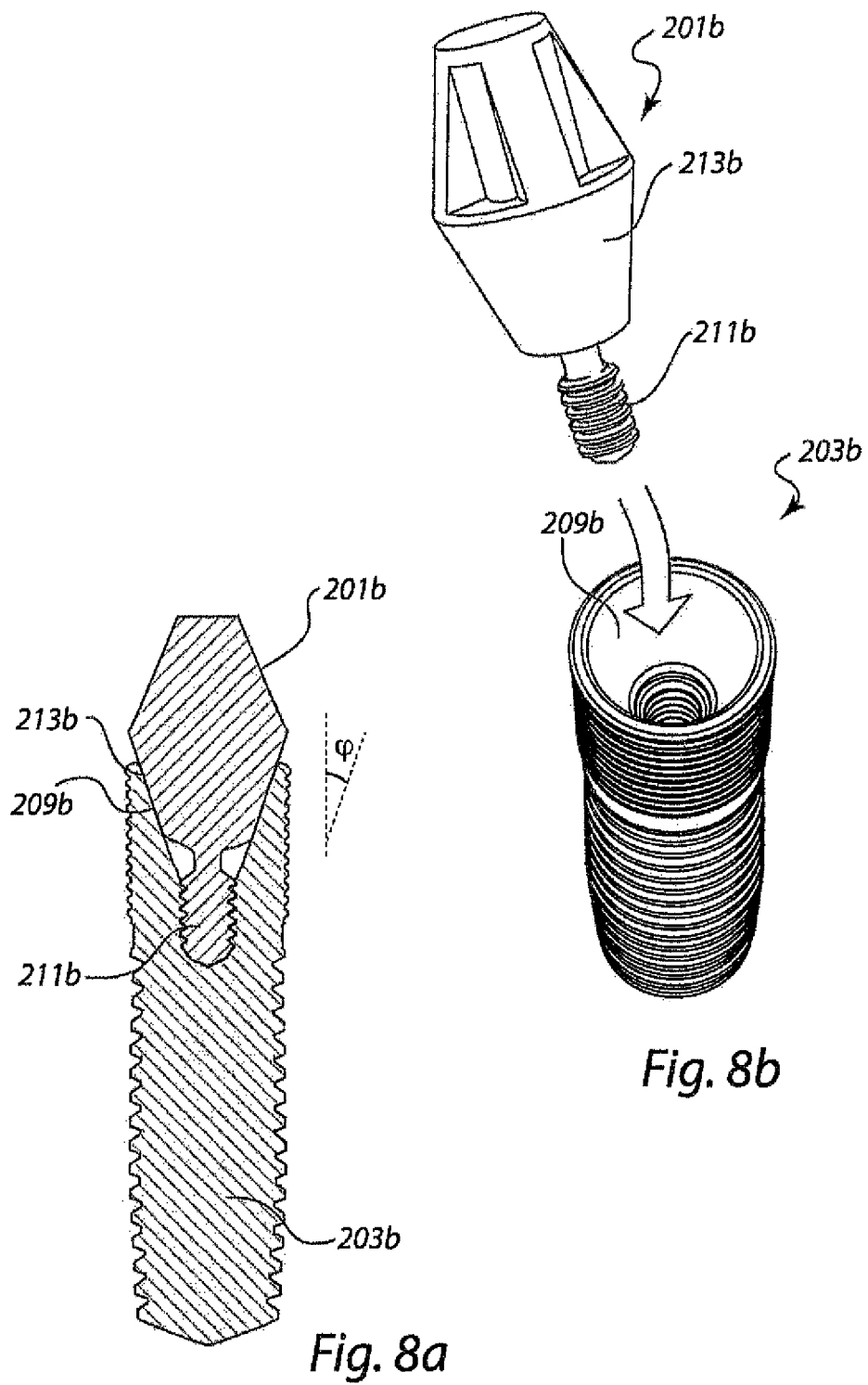
FIGS. 8*a-b* illustrate a set of dental components comprising a subset of male dental components and a subset of female dental components according to at least some example embodiments.
Figures 9A, 9B:
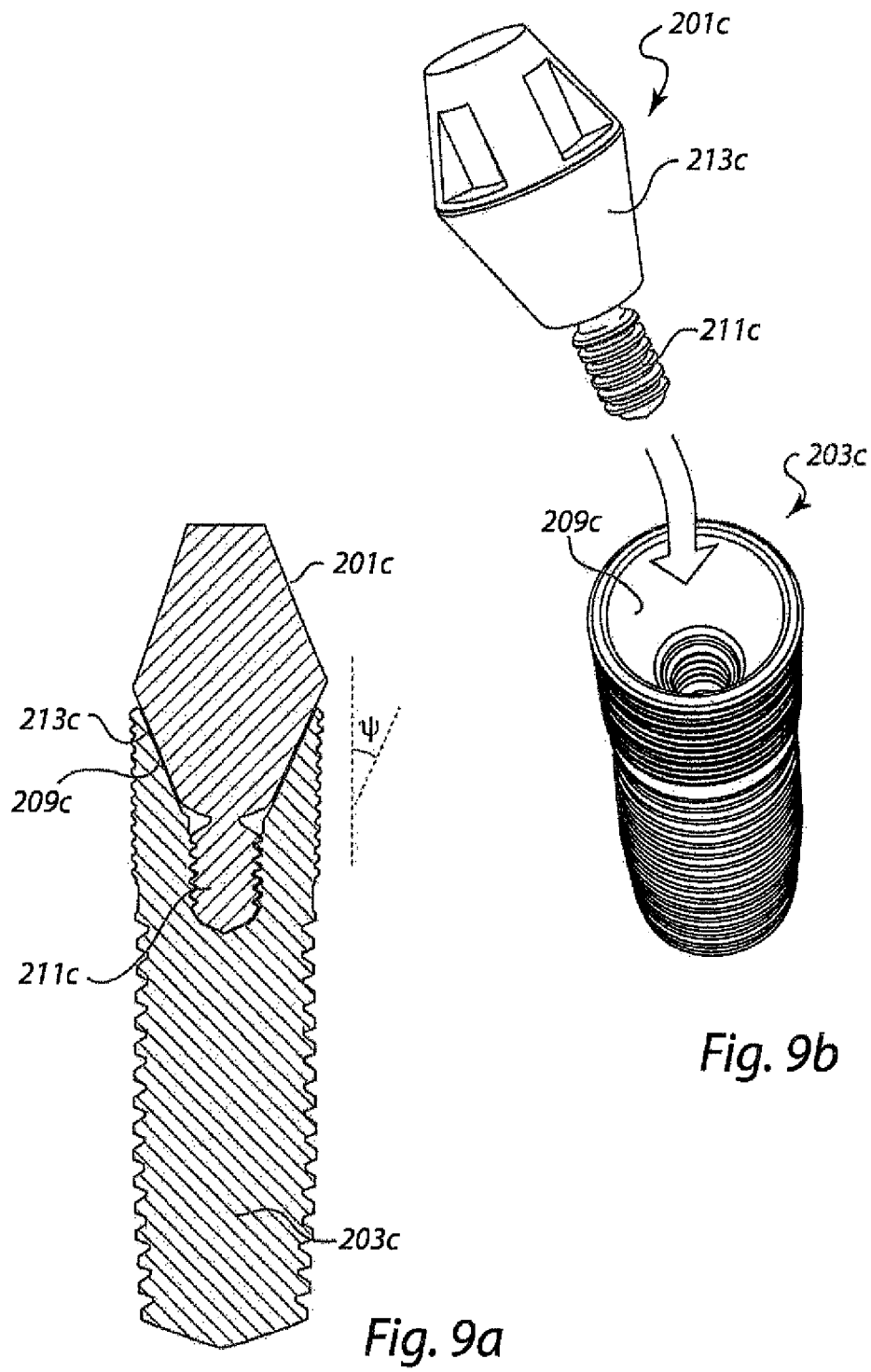
FIGS. 9*a-b* illustrate a set of dental components comprising a subset of male dental components and a subset of female dental components according to at least some example embodiments.

FIGS. 8a-8b illustrate a second abutment 201b having a threaded portion 211b with a somewhat wider core than the core of the first abutment 201a. Thus, the threaded portion 211b of the second abutment 201b is stronger and does therefore not require as high friction as the first abutment 201a. Consequently, the seat-mating portion 213b of the second abutment 201b and the mating seat 209b of the second fixture 203b form a larger angle φ with respect to the central axis compare to the angle θ presented by the first abutment 201a and first fixture 203a. Similarly, since the threaded portion 211c of the third abutment 201c in FIG. 9a-9b has an even larger diameter, the acute angle ψ formed by the seat-mating portion 213c of the third abutment 201c and the seat 209c of the third fixture 203c is even larger than said angle φ of the second abutment 201b and second fixture 203b.

Figures 10A, 10B:
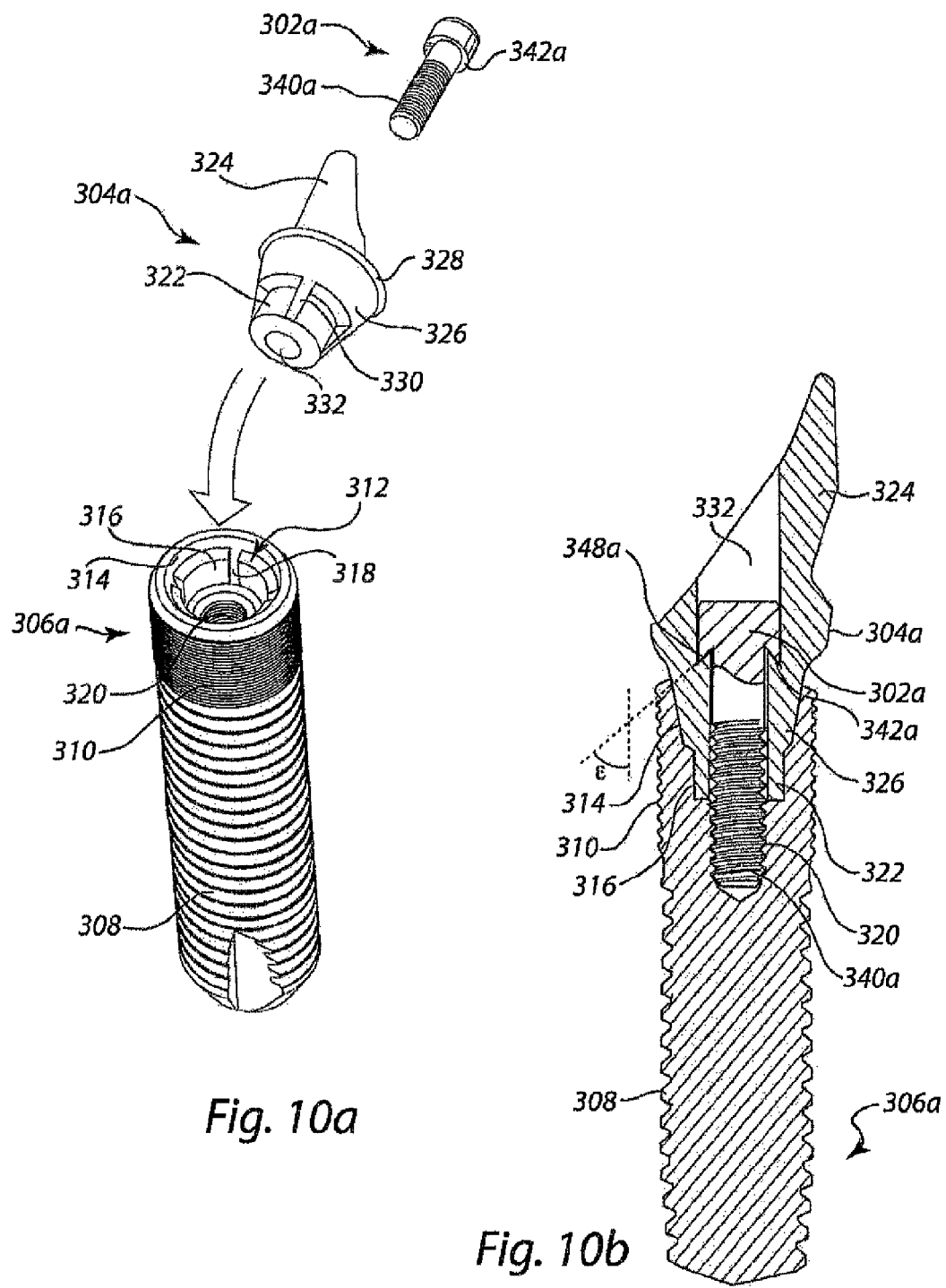
FIGS. 10*a*-10*b* illustrate a male dental component and a female dental component which may be comprised in a set of dental components according to at least some example embodiments.

FIGS. 10a-10b illustrate a male dental component and a female dental component which may be comprised in a set of dental components according to at least some example embodiments. The male dental component is here in the form of an abutment screw 302a which is adapted to be joined to a female dental component, here in the form of an abutment 304a, in order to fasten the abutment 304a to a fixture 306a.

The features in FIGS. 10a-10b substantially correspond to those that have been illustrated for the components in FIGS. 1a-1b. Therefore, to corresponding features the numeral value 300 has been added. The only noticeable difference between the embodiments in FIGS. 1a-1b and FIGS. 10a-10b is that in FIGS. 1a-1b the seat-mating portion 42a and the mating seat 48a are tapering in the apical direction, while in FIGS. 10a-10b the seat-mating portion 342a and the mating seat 348a are tapering in the coronal direction. The seat-mating portion 342a and the mating seat 348a form an angle ε in relation to the central axis. If the acute angle ε in FIG. 10b has the same value as the acute angle α in FIG. 1b, then the friction between the abutment screw 302a and abutment 304a may be the same as the friction between abutment screw 2a and abutment 4a. It should be noted that (apart from 90° angles) it is the acute angle (<90°) that is formed between the seat/seat-mating portion and the central axis that is to be considered, and consequently not the obtuse angle formed relative to the central axis.

Thus, similarly to the variations in the set presented in FIGS. 1a-b to 3a-b, a set may in addition to the components in FIG. 10a-10b include other component pairs with different angles on coronally tapering seats/seat-mating portions, to compensate for different core thicknesses of the male dental components.

The coronally directed tapering of the seat 348a and seat-mating portion 342a illustrated in FIGS. 10a-10b may advantageously be used for ceramic abutments, since in this configuration the seat-mating portion 342a will provide an inwardly directed pressure on the seat 348a which reduces the risk of fracturing the relatively fragile ceramic abutment.

Furthermore, it is also conceivable to provide a set of dental components in which some of the male/female component pairs have coronally tapering seat-mating portions and seats, while others have apically tapering seat-mating portions and seats, the formed angle relative to the central axis being dependent on the dimension of the respective core of the threaded portion of the male dental component.

Although the illustrated embodiments have shown that the seat-mating portion of the male dental component has the same angle relative to the central axis as the mating seat of the associated female dental component, an alternative would be to allow the seat-mating portion and the seat to have different angles and still be able to provide different frictional properties for different components.

The invention claimed is:

1. A set of dental components, comprising
a subset of male dental components comprising
a first male dental component and a second male dental component,
a subset of female dental components comprising
a first female dental component and a second female dental component, each having an engagement portion that includes a generally cylindrical enveloping surface having a plurality of radial projections spaced therearound, and a subset of female dental fixtures adapted to be inserted into the jawbone comprising a first female dental fixture and a second female dental fixture,
wherein said first male dental component is connected to said first female dental component, the first male dental component comprising a head, a threaded portion having a core provided with an external thread and a first non-threaded seat-mating portion extending between the head and the threaded portion, the first non-threaded seat-mating portion defining a first contact surface area and forming a non-zero angle $\alpha$ that is less than 90° in relation to the longitudinal central axis of the first male dental component,
wherein said second male dental component is connected to said second female dental component, the second male dental component comprising a head, a threaded portion having a core provided with an external thread and a second non-threaded seat-mating portion extending between the head and the threaded portion, the second non-threaded seat-mating portion defining a second contact surface area and forming a non-zero angle $\beta$ that is less than 90° in relation to the longitudinal central axis of the second male dental component,
wherein the first contact surface area is larger than the second surface contact area and the non-zero angle $\alpha$ is less than the non-zero angle $\beta$,
wherein the core of the threaded portion of said first male dental component has a smaller diameter than the core of the threaded portion of said second male dental component, and wherein, when the male dental components are finally tightened with the same torque to their respective female dental components, the friction between said first male dental component and said first female dental component is higher than the friction between said second male dental component and said second female dental component,
wherein the core of the threaded portion of said first male dental component is received by a threaded recess disposed apically of an intermediate wall section having a plurality of radially extending recesses of the first female dental fixture and the core of the threaded portion of said second male dental component is received by a threaded recess disposed apically of an intermediate wall section having a plurality of radially extending recesses of the second female dental fixture,
wherein each non-threaded seat-mating portion is located coronally of said threaded portion and each female dental component comprises a seat for receiving said non-threaded seat-mating portion of the respective male dental component, wherein said non-threaded seat-mating portion and said seat each forms the non-zero angles $\alpha$ and $\beta$ in relation to the longitudinal central axis of the respective dental component, and wherein, when the male dental components are finally tightened with the same torque to their respective female dental components, the friction between the first non-threaded seat-mating portion of the first male dental component and the seat of the first female dental component is higher than the friction between the second non-threaded seat-mating portion of the second male dental component and the seat of the second female dental component,
wherein the coefficient of friction between said contact surface of the first male dental component and its mating first female dental component is higher than the coefficient of friction between said contact surface of the second male dental component and its mating second female dental component,
wherein said female dental components are abutments adapted to be connected to the respective dental fixture insertable into a jawbone, wherein said male dental components are abutment screws for fastening the respective mating abutment to the respective dental fixture.

* * * * *